US00PP08827P

United States Patent [19]

Hatten

[11] Patent Number: Plant 8,827

[45] Date of Patent: Jul. 12, 1994

[54] BOUGAINVILLEA HYBRID CV. BLUSHING BEAUTY

[75] Inventor: William A. Hatten, Mobile, Ala.

[73] Assignee: Hatten's Nursery, Inc., Mobile, Ala.

[21] Appl. No.: 57,280

[22] Filed: Apr. 30, 1993

[51] Int. Cl.[5] ..... A01H 5/00

[52] U.S. Cl. ..... Plt./67.7

[58] Field of Search ..... Plt. 67.7

*Primary Examiner*—James R. Feyrer

*Attorney, Agent, or Firm*—Tilton Fallon Lungmus

[57] ABSTRACT

A new and distinct Bougainvillea particularly distinguished from other Bougainvillea plants by its pale pink blush-colored flower bracts. The bracts having a trace of white on each side of a green midrib; its peduncles, pedicils and young stems are yellowish, with its young leaves exhibiting a definite variegation of light and dark green.

1 Drawing Sheet

BACKGROUND OF THE NEW PLANT

This invention relates to a new and distinct selection of Bougainvillea, a member of the Nyctaginaceae family, which was discovered by me as a sport occurring in a group of the Bougainvillea Hybrid cultivar Juanita Hatten (unpatented). This sport was discovered in the summer of 1989 in Mobile, Ala. in one of the commercial greenhouses of Hatten's Nursery, Inc. as a spontaneous bud sport growing on a potted specimen plant of the Bougainvillea Hybrid cv. Juanita Hatten. Because of the high quality growth habit, and the unusual coloration of the flower bracts of this plant, it was selected by me for propagation. Asexual reproduction of this plant by cutting at my nursery in Mobile, Ala. has continued from generation to generation and shows that its characteristics remain fixed and that its homogeneity can be assured.

BRIEF DESCRIPTION OF THE DRAWING

The accompanying photographic drawing shows a typical specimen of the plant, in full bloom, the color rendition being as nearly true to that herein specified as is reasonably possible to obtain by professional photographic procedures.

DESCRIPTION OF THE NEW PLANT

The following is a detailed description of my new Bougainvillea cultivar based upon observation of plants grown in greenhouse as well as outdoors at Mobile, Ala. and blooming during the current year. The color designations stated herein are according to R.H.S. Colour Chart published by The Royal Horticultural Society of London, England. The illustration clearly shows the unusual pink blush and white-colored bracts, the light and dark green variegation of the foliage, and its yellowish peduncles and stems.

THE PLANT

Origin: Sport.

Parentage: Juanita Hatten (unpatented) originated in 1982. cv. Juanita Hatten is a well-known commercial variety.

Classification: Bougainvillea.

Family: Nyclaginaceae.

Species: Hybrid; species parentage unknown.

Form: Medium vining shrub, well suited for pot, hanging basket and tub culture. Also suitable for landscape plantings in frost-free areas. This plant is cascading with long, leafy, wand-like branches.

Growth habit: The high quality growth is exhibited by its compact growth and free branching habit. Distance between leaf nodes is 1 to 4 cm. The plant is free branching, especially after pruning. Two to four lateral branches are produced after pinching or pruning the terminal bud on any stem. This makes the plant suitable for hanging basket or container production.

When grown in a container, the overall growth of the main branches should be less than one meter per year. After one year's growth, the diameter of the lateral branches varies from 6 to 10 mm at their base, tapering to 2 mm at the terminal bud. The shape is mounding and cascading. Pruning is necessary once or twice per year. The plant is very tolerant of pruning and its shape and appearance is enhanced by several prunings per year. Two to four lateral branches will be produced on each stem that is pruned. The density of the canopy and number of flowers produced is vastly improved with pruning.

Training or staking is not required when grown in hanging baskets, or in pots up to 5 gallon capacity. However, the plant is readily adaptable to training on a trellis, or training as a tree-form specimen if staked. When cv. Blushing Beauty is grown in a 10" hanging basket or in a 1-5 gallon container, the plant requires pruning once or twice a year, depending on the desired appearance.

The plant is very tolerant of pruning and may be pruned to within 25 cm. of the soil line, provided that several lateral branches and a reasonable amount of foliage remain. Soft pruning or pinching can be used to produce more lateral branches and foliage. This method produces a full and compact plant that can be maintained in a container for a number of years. As flowering occurs on new growth, pinching and pruning results in more lateral branches, a greater display of color and slower lateral growth. Outdoor plantings in frost free areas should also be treated as above. If left unpruned, the limbs will grow between one and two meters per year depending on prevailing conditions.

Flowering: Profuse and free flowering in Southern Alabama from December to October.

THE FLOWER

Corolla: Absent.

Calyx: Salverform, tubular: 1.6 cm long (+ −0.2 cm). All pubescence of the calyx is puberulent with short, ascending, curved hairs.

*Outer surface.*—Sparsely puberulent, tube green with five longitudinal ribs.

*Inner surface.*—Glabrous and lustrous, five shallow lobes, upper surface of the lobes white and sparsely puberulent, lower surface of the lobes white with a green vein and sparsely puberulent.

*Calyx petaloids.*—Number: Ten. Arrangement: Attached in fused pairs between the calyx lobes. Color: White. Character: Inconspicuously puberulent to glabrous.

Arrangement: Flowers in clusters of three, the pedicil of each adnate to the midrib of a showy bract up to the base of the calyx tube, the three bracts closely appressed at their bases and attached at the top of the ultimate branches of the peduncles.

Flower bract:

*Color.*—Predominently blush pink 72-C with a midrib of agathia green 142-B, and a trace of white 157-C on each side of the midrib. The pink color intensifies from the base of the bract to the top edge, with the darkest color being at the upper edge of the bract. The obvious difference between cv. Juanita Hatten and cv. Blushing Beauty is the color of the bracts. The bract color of cv. Juanita is uniformly red-purple 64-B, while the bract color of cv. Blushing Beauty is predominately red-purple 72-C with a midrib of 142-B and a trace of 157-C on each side of the midrib. Also, the pink color intensifies from the base of the bract to the top edge, with the darkest color being at the top edge of the bract. Non-persistant.

*Size.*—Length: 3.8 to 4.5 cm in length. Width: 2.7 to 3.5 cm in width. Ovate to broadly elliptic.

*Margins.*—Undulate, glabrous.

Peduncles: Varying from yellow green 153-D to red 37-A. Elongated, and rising from the leaf axils inconspicuously puberulent with short ascending curved hairs.

Pedicels: Varying from yellow green 153-D to red 37-A. Elongated, and rising from the leaf axils inconspicuously puberulent with short ascending curved hairs. Bougainvillea cv. Juanita Hatten and Bougainvillea cv. Blushing Beauty share the following characteristics: peduncles, pediceles and young steams are yellowish.

Foilage:

*Arrangement.*—Alternate.

*Size*—Foilage size varies depending upon age. Length: 5.0 to 8.5 cm in length. Width: 3.5 to 5.2 cm in width.

*Color.*—New growth variegated with yellow green 144-C along the midrib and green 137-C along outer portions. Older leaves uniformly green 137-A. Young leaves of both Bougainvillea cv. Juanita Hatten and Bougainvillea cv. Blushing Beauty exhibit a definite variegation of light and dark green. Both cultivars are also very floriferous.

Shape: Ovate to broadly elliptic, apex acute to accuminate.

Margins: Entire, occasionally slightly undulate.

Pubescence: Sparsely and minutely puberulent, with short ascending curved hairs on upper and lower surfaces, primarily on midrib and larger veins.

Spines: Yellowish, slightly recurved, borne in the axils of leaves.

Bark: Mature bark is smooth to slightly rough and woody ranging in color from 177-C to 177-A.

REPRODUCTIVE ORGANS

Stamens:

*Calyx.*—The color of the outer surface of the calyx tube of cv. Blushing Beauty is green 138-B, while the color of the outer surface of the calyx tube on cv. Juanita Hatten is red-purple 64-A.

*Number.*—Eight.

*Form.*—Included in the calyx tube on unequal filaments, fused only at their extreme bases.

Pistil: One. Containing one ovule, ovary stipitate, style lateral shorter than surrounding stamen filaments.

Fertility: Bougainvillea cv. Blushing Beauty is pollen and ovary sterile, probably due to interspecific hybridation in its remote background, As is typical of Bougainvilleas, the intensity of the bract color is dependent upon the climate and quality and intensity of the sunlight. All observations stated herein are based on Bougainvillea Hybrid C.V. Blushing Beauty growing and blooming in mid summer in Mobile, Ala. in a greenhouse covered with 6 mm UV resistant polyethylene sheeting. Bougainvilleas Hybrid CV. Blushing Beauty differs from its parent, Bougainvillea Hybrids CV Juanita Hatten in the blush pink coloration of its flower bracts, with a trace of white on each side of a green midrib, whereas CV Juanita Hatten's flower tracts are a deep red. Also, the outer surface of the calyx tubes of Bougainvillea Hybrid cv. Blushing Beauty are green whereas Bougainvillea Hybrid cv. Juanita Hatten's are redish-purple.

I claim:

1. A new and distinct variety of Bougainvillea plant as substantially shown and herein described, characterized by its unique combination of a very floriferous habit, pink-blush flower bracts with a trace of white on each side of a green midrib, the green outer surface of its calyx tubes, and the light and dark green variegation of its foilage.

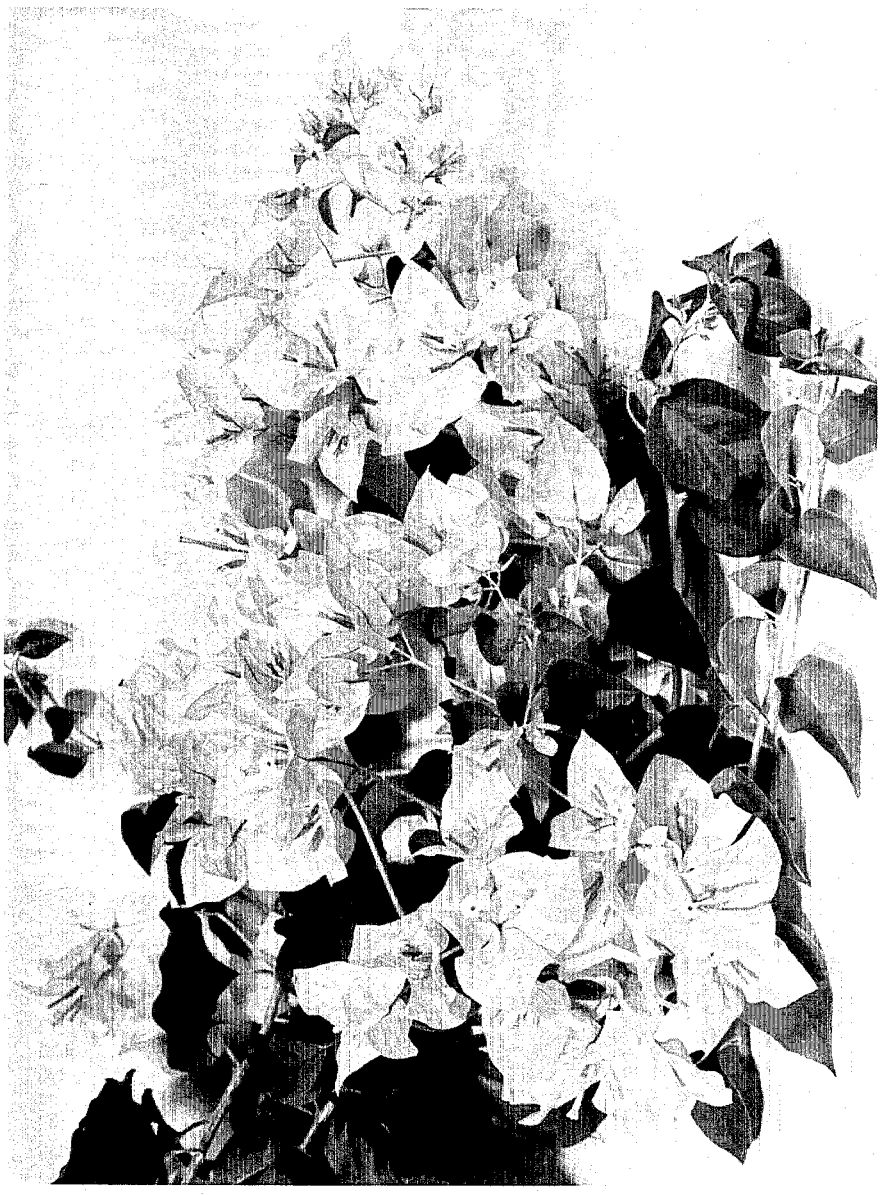

* * * * *